(12) United States Patent
Morita et al.

(10) Patent No.: US 9,326,990 B2
(45) Date of Patent: May 3, 2016

(54) HEART FAILURE SUPPRESSING AGENT

(75) Inventors: Hiroyuki Morita, Bunkyo-ku (JP);
Ryozo Nagai, Bunkyo-ku (JP); Atsuko Nakayama, Bunkyo-ku (JP); Tadashi Hashimoto, Chiyoda-ku (JP)

(73) Assignees: THE UNIVERSITY OF TOKYO, Tokyo (JP); THERAVALUES CORPORATION, Tokyo (JP)

( * ) Notice: Subject to any disclaimer, the term of this patent is extended or adjusted under 35 U.S.C. 154(b) by 107 days.

(21) Appl. No.: 14/233,581

(22) PCT Filed: Jul. 19, 2012

(86) PCT No.: PCT/JP2012/068382
§ 371 (c)(1),
(2), (4) Date: Jan. 17, 2014

(87) PCT Pub. No.: WO2013/012049
PCT Pub. Date: Jan. 24, 2013

(65) Prior Publication Data
US 2014/0194372 A1   Jul. 10, 2014

(30) Foreign Application Priority Data

Jul. 20, 2011 (JP) ................. 2011-158920
Sep. 6, 2011 (JP) ................. 2011-193508
May 22, 2012 (JP) ................. 2012-116387

(51) Int. Cl.
| | |
|---|---|
| A61K 31/7048 | (2006.01) |
| A61K 31/352 | (2006.01) |
| A61K 31/353 | (2006.01) |
| C07D 311/30 | (2006.01) |
| A23L 1/30 | (2006.01) |
| C07H 17/07 | (2006.01) |

(52) U.S. Cl.
CPC ............ *A61K 31/7048* (2013.01); *A23L 1/3002* (2013.01); *A61K 31/352* (2013.01); *A61K 31/353* (2013.01); *C07D 311/30* (2013.01); *C07H 17/07* (2013.01)

(58) Field of Classification Search
None
See application file for complete search history.

(56) References Cited

FOREIGN PATENT DOCUMENTS

| | | |
|---|---|---|
| JP | 9-143070 | 6/1997 |
| JP | 10-95732 | 4/1998 |

OTHER PUBLICATIONS

Rump et al., Gen. Pharamcol., vol. 25 (6), 1994, pp. 1137-1142.*
International Search Report and Written Opinion of the International Searching Authority issued Oct. 9, 2012, in PCT/JP2012/068382, filed Jul. 19, 2012.
Gloria Gutiérrez-Venegas, et al., "The flavonoids luteolin and quercetagetin inhibit lipoteichoic acid actions on H9c2 cardiomyocytes", International Immunopharmacology, vol. 10, 2010, pp. 1003-1009.
Ichiro Shiojima, "AKT Signaling and Cardiac Hypertrophy", Molecular Cardiovascular Disease, vol. 7, No. 6, 2006, pp. 574-579 (with partial English translation).
Syed Haq, et al., "Differential Activation of Signal Transduction Pathways in Human Hearts With Hypertrophy Versus Advanced Heart Failure", Circulation, vol. 103, Feb. 6, 2001, pp. 670-677.
Hideo A. Baba, et al., "Dynamic regulation of MEK/Erks and Akt/GSK-3β in human end-stage heart failure after left ventricular mechanical support: myocardial mechanotransduction-sensitivity as a possible molecular mechanism", Cardiovascular Research, vol. 59, 2003, pp. 390-399.
A. F. E. Rump, et al., "Functional and Antiischemic Effects of Luteolin-7-Glucoside in Isolated Rabbit Hearts", Gen. Pharmacol., vol. 25, No. 6, 1994, pp. 1137-1142.
Mine Sou, et al., "Disease-specific nutritional management focusing on infusion, learning with cases; Infusion Management of Cardiac Failure", Nutrition Care, vol. 2, No. 6, 2009, pp. 612-616 (with English Abstract).
Ming-Jivan Wu, et al., "Antioxidant Activity of *Glossogyne tenuifolia*" Journal of Agricultural and Food Chemistry, vol. 53, No. 16, 2005, pp. 6305-6312.
Jung-Suk Choi, et al., "Flavones Mitigate Tumor Necrosis Factor-α-Induced Adhesion Molecule Upregulation in Cultured Human Endothelial Cells: Role of Nuclear Factor-$_κ$B[1]", The Journal of Nutrition, vol. 134, 2004, pp. 1013-1019.
Takashi Shibuya, "Pathophysiology of Aortic Aneurysm", Molecular Cardiovascular Disease, vol. 8, No. 1, 2007, pp. 22-26 (with partial English translation).
Kazufumi Nakamura, et al., "Inhibitory Effects of Antioxidants on Neonatal Rat Cardiac Myocyte Hypertrophy Induced by Tumor Necrosis Factor-α and Angiotensin II", Circulation, vol. 98, Aug. 25, 1998, pp. 794-799.

* cited by examiner

*Primary Examiner* — Traviss C McIntosh, III
(74) *Attorney, Agent, or Firm* — Oblon, McClelland, Maier & Neustadt, L.L.P.

(57) ABSTRACT

Provided are a medicine and a food product that suppress a heart disease such as cardiomegaly and heart failure. Specifically provided is an agent for suppressing a heart disease selected from heart failure, cardiac fibrosis, ventricular wall thickening and cardiomegaly, which comprises luteolin or a derivative thereof as an active ingredient.

24 Claims, 12 Drawing Sheets

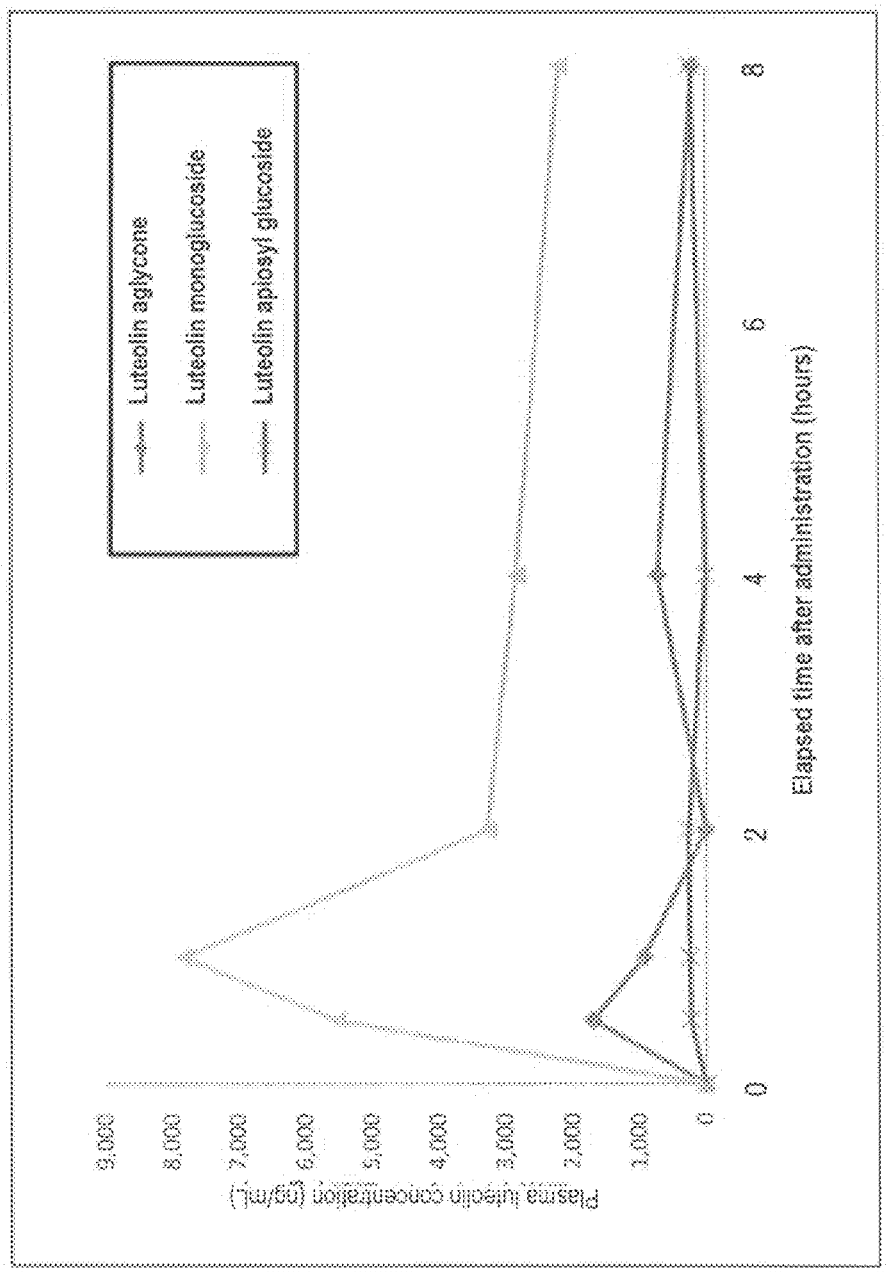

HEART FAILURE SUPPRESSING AGENT

TECHNICAL FIELD

The present invention relates to a medicine that suppresses heart diseases such as cardiac fibrosis, ventricular wall thickening, cardiomegaly and heart failure and aneurysm.

BACKGROUND ART

When cardiomegaly is prolonged, the risk of heart failure, sudden death, and the like increases, and thus, it is important to suppress cardiomegaly in order to prevent and suppress heart failure. Such cardiomegaly is classified into those due to physiological conditions by exercise stress or the like, and those due to non-physiological conditions by pathological stress reaction of myocardium.

On the other hand, reactive oxygen (Reactive Oxygen Species: ROS) is known to participate in signal transduction of cell growth in many cells including those of the cardiovascular system. It is proved that reactive oxygen mediates the myocardial cell hypertrophy by angiotensin II and TNF-$\alpha$ in the myocardial cell, and it is shown that reactive oxygen participates in signal transduction of the myocardial cell hypertrophy as a second messenger (Non-Patent Literature 1). The relation between reactive oxygen and cardiomegaly is also reported at the cell level and the animal level, and it is known that reactive oxygen is promptly produced after stimulation by TNF-$\alpha$, angiotensin II, endothelin-I or phenylephrine, which is a hypertrophy stimulator. In addition, sustained subcutaneous administration of angiotensin II is widely known as a cardiomegaly model, and it is known that reactive oxygen is also produced in the myocardium in this model.

Cardiomegaly, particularly cardiomegaly due to non-physiological conditions by pathological stress reaction of the myocardium is usually characterized by myocardial fibrosis and ventricular wall thickening. Persistent overstress to the myocardium by long term hypertension or abnormal stress to the myocardium after the myocardial infarction is often a cause for cardiomegaly. It is known that prolonged cardiomegaly leads to failure of the function of the heart as a pump, resulting in heart failure.

Statin, edaravone, $\beta$-blockers or the like is expected as a drug for such cardiomegaly, but the efficiency thereof has not been confirmed yet.

In addition, aneurysm is the most cause for subarachnoid hemorrhage, but the cause for the onset has not been clearly determined yet. Examples of a risk factor for aneurysm include hypertension and arteriosclerosis, but it is not clear whether they are a direct cause or not. As a therapeutic approach for aneurysm other than surgery, an antihypertensive drug is used only to prevent the progress thereof.

CITATION LIST

Patent Literature

Non-Patent Literature 1: Circulation 98: 794-799, 1998

SUMMARY OF INVENTION

Technical Problem

An object of the present invention is to provide a medicine and a food product that suppress heart diseases such as cardiomegaly and heart failure, and aneurysm.

Solution to Problem

Now, the present inventors investigated extensively to find an ingredient that suppresses cardiomegaly or aneurysm, and has high safety. As a result, the present inventors found that luteolin or a derivative thereof, which is one kind of yellow pigment flavonoids contained in a food plant, remarkably suppresses cardiac fibrosis, ventricular wall thickening, cardiomegaly and aneurysm without influence on the blood pressure in a rat model of angiotensin II-sustained administration, and is useful as an agent for preventing and suppressing heart failure, or an agent for suppressing aneurysm, and thus completed the present invention.

The present inventors further found that among the luteolin or a derivative thereof, particularly luteolin-7-O-glucoside has high oral absorption, and is useful as a medicine or a food product for oral intake.

Specifically, the present invention provides an agent for suppressing a heart disease selected from the cardiac fibrosis, ventricular wall thickening, cardiomegaly and heart failure, which comprises luteolin or a derivative thereof as an active ingredient.

In addition, the present invention provides an agent for suppressing aneurysm, which comprises luteolin or a derivative thereof as an active ingredient.

In addition, the present invention provides use of luteolin or a derivative thereof for manufacture of an agent for suppressing a heart disease selected from the cardiac fibrosis, ventricular wall thickening, cardiomegaly and heart failure.

In addition, the present invention provides use of luteolin or a derivative thereof for manufacture of an agent for suppressing aneurysm.

In addition, the present invention provides luteolin or a derivative thereof for use in suppressing a heart disease selected from cardiac fibrosis, ventricular wall thickening, cardiomegaly and heart failure.

In addition, the present invention provides luteolin or a derivative thereof for use in suppressing aneurysm.

In addition, the present invention provides a method of suppressing a heart disease selected from cardiac fibrosis, ventricular wall thickening, cardiomegaly and heart failure, the method comprising administering an effective amount of luteolin or a derivative thereof.

In addition, the present invention provides a method of suppressing aneurysm, comprising administering an effective amount of luteolin or a derivative thereof.

Furthermore, the present invention provides a composition for oral intake comprising luteolin-7-O-glucoside.

Advantageous Effects of Invention

Luteolin or a derivative thereof remarkably suppresses cardiac fibrosis, ventricular wall thickening and cardiomegaly, which are a causal symptom for heart failure, and thus is useful as a medicine or a food product for preventing and/or suppressing heart failure. In addition, luteolin or a derivative thereof remarkably suppresses aneurysm, and thus is useful as a medicine or a food product for preventing and/or suppressing aneurysm. Meanwhile, it is understood that the action described above of luteolin or a derivative thereof is not an action by lowering the blood pressure from the fact that luteolin or a derivative thereof does not have influence on the blood pressure in a dose where the above-described action is exerted in an angiotensin II-continuous infusion model. In addition, luteolin or a derivative thereof has high safety and allows long term intake, and thus is useful as an agent for preventing particularly cardiomegaly, heart failure and aneurysm.

BRIEF DESCRIPTION OF DRAWINGS

FIG. 12 illustrates the plasma concentration of luteolin and a glycoside thereof.

DESCRIPTION OF EMBODIMENTS

Figure 1:
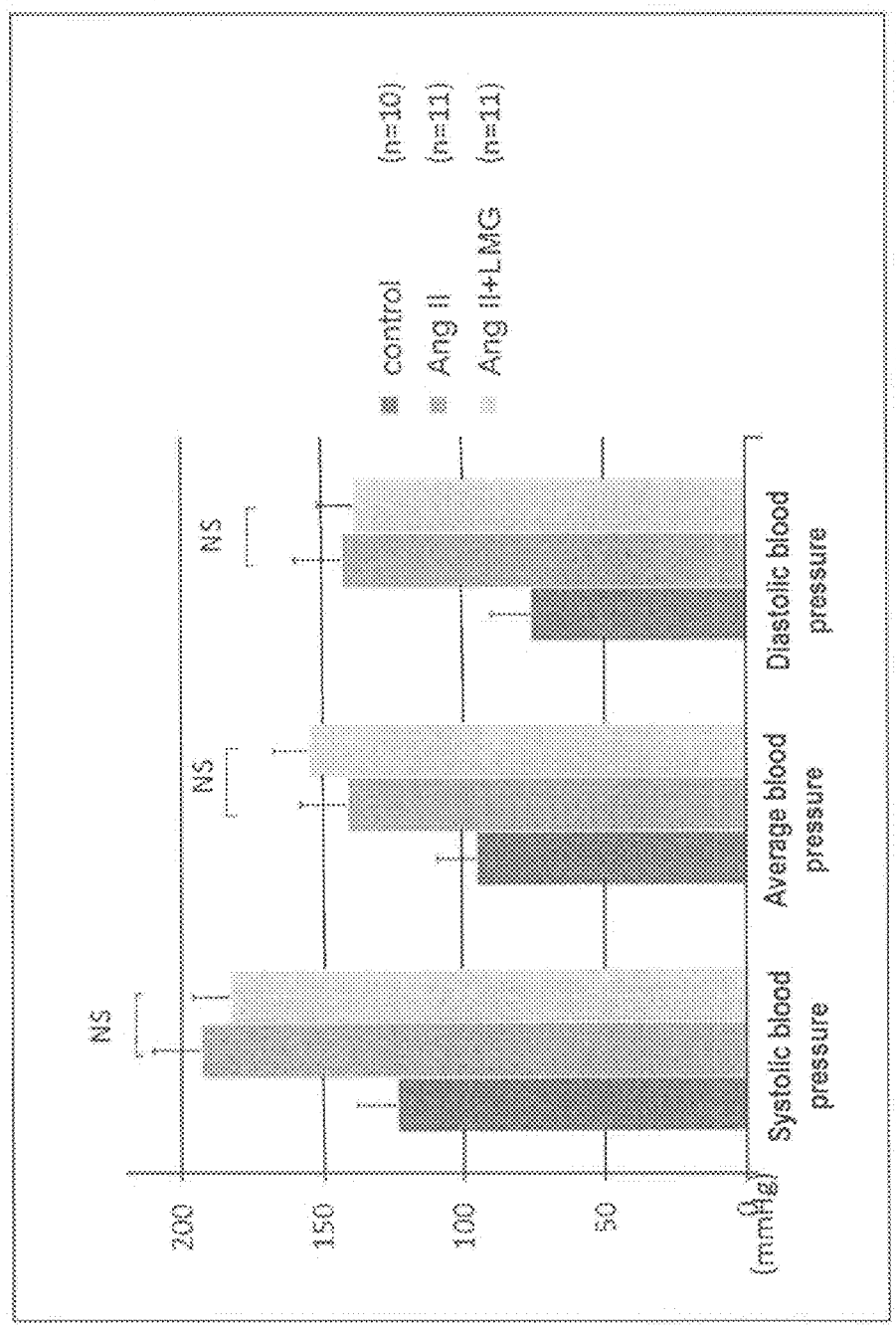
FIG. 1 illustrates the action of luteolin glycoside on the blood pressure.

An active ingredient of an agent for suppressing a heart disease selected from the cardiac fibrosis, ventricular wall thickening, cardiomegaly and heart failure, or an agent for suppressing aneurysm of the present invention (hereinafter, also collectively referred to as an agent for suppressing heart failure and the like) is luteolin or a derivative thereof. Luteolin or a derivative thereof is one kind of yellow pigment flavonoids represented by Formula (1) described below:

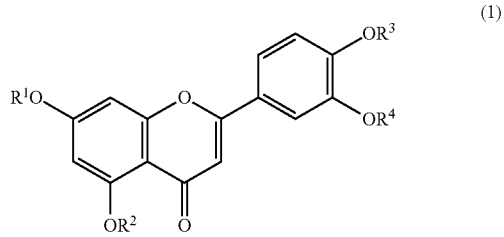

wherein $R^1$ to $R^4$ represent each independently, a hydrogen atom, an alkyl group, a sulfo group or a sugar residue.

Among them, particularly luteolin or a glycoside thereof is particularly preferred.

Examples of the alkyl group represented by $R^1$ to $R^4$ include $C_{1-4}$ alkyl groups, preferably a methyl group, an ethyl group, an n-propyl group and an isopropyl group, more preferably a methyl group. The sulfo group is a group represented by $-SO_3H$. Examples of the sugar that constitutes the sugar residue represented by $R^1$ to $R^4$ include monosaccharides such as glucose, galactose, xylose, mannose and glucuronic acid; disaccharides such as apiosyl glucoside, maltose, cellobiose and gentiobiose; and acetylated forms, malonylated forms or the like of these monosaccharides or disaccharides. Among these sugar residues, a monosaccharide- or disaccharide-derived residue is more preferred.

As the luteolin or a glycoside thereof, luteolin ($R^1$ to $R^4$=H), and luteolin-7-O-glycoside ($R^1$=monosaccharide or disaccharide, $R^2$ to $R^4$=H) are preferred, with being more preferably luteolin and luteolin-7-O-glucoside ($R^1$=glucose residue and $R^2$ to $R^4$=H), particularly preferably luteolin-7-O-glucoside from the viewpoint of the oral absorption.

The luteolin or a derivative thereof is known to be contained in foods of Solanaceae, Pedaliaceae, Lamiaceae, Asteraceae, Apiaceae, Brassicaceae, Poaceae, Fabaceae, Rosaceae, Caprifoliaceae, Theaceae, and the like. Examples of the plant of Solanaceae include plants of the genus *Capsicum*. Among them, the luteolin or a derivative thereof is contained in large quantities in chili pepper, green pepper, paprika and the like. Examples of the plant of Pedaliaceae include plants of the genus *Sesamum*. Among them, the luteolin or a derivative thereof is contained in large quantities in *sesamum* indicum. In addition, examples of the plant of Lamiaceae include plants of the genus *Perilla* such as wild sesame and *perilla*, the genus *Mentha* such as mint and peppermint, the genus *Rosmarinus* such as rosemary, the genus *Thymus* such as Thyme, the genus *Origanum* such as oregano and the genus *Salvia* such as sage. In addition, examples of the plant of Asteraceae include plants of the genus *Chrysanthemum* such as crown daisy, the genus *Lactuca* such as lettuce, the genus *Matricaria* such as chamomile and the genus *Taraxacum* such as dandelion. Examples of the plant of Apiaceae include plants of the genus *Apium* such as celery, the genus *Petroselinum* such as parsley, the genus *Angelica* such as *Angelica keiskei*, and the genus *Daucus* such as carrot. Examples of the plant of Brassicaceae include plants of the genus *Brassica* such as broccoli and cabbage. Examples of the plant of Poaceae include sugarcane. Examples of the plant of Fabaceae include peanut, rooibos and the like. Examples of the plant of Rosaceae include *Malus pumila*. Examples of the plant of Caprifoliaceae include Japanese honeysuckle and the like. In addition, examples of the plant of Theaceae include tea tree and the like. The extraction part is preferably an edible part of these plants.

In extraction of luteolin or a derivative thereof from these food plants, water or an organic solvent is preferably used, for example, hot water, alcohols such as ethanol, esters such as ethyl acetate, ethers such as diethyl ether and dioxane, halogenated hydrocarbons such as chloroform and dichloromethane, ketones such as acetone, or the like. Among them, extraction using water or ethanol is particularly preferred. The extraction is preferably performed at a temperature of 0° C. to the boiling point of the solvent or lower for 1 hour to 72 hours. The extract may be further purified with column chromatography or the like. In addition, as luteolin or a derivative thereof, a commercialized product may be used.

In addition, luteolin-7-O-glucoside (7-O-(β-D-glucosyl luteolin) may be obtained from acid hydrolysis of luteolin-7-O-apiosyl (1-2)-glucoside (JP-A 2008-201795).

In the agent for suppressing heart failure and the like of the present invention, luteolin or a derivative thereof may be blended, or a plant extract containing luteolin or a derivative thereof may be blended.

Luteolin or a derivative thereof exhibits excellent suppression action for cardiac fibrosis, suppression action for ventricular wall thickening, suppression action for cardiomegaly, suppression action for heart failure and suppression action for aneurysm without influence on the blood pressure in models of cardiomegaly, heart failure and aneurysm by angiotensin II-continuous infusion, as shown in Examples described below. Accordingly, luteolin or a derivative thereof is useful particularly as an agent for suppressing cardiomegaly, an agent for suppressing heart failure, and an agent for suppressing aneurysm.

Herein, the suppressing agent encompasses both of improvement of the symptoms of these diseases, and lowering of the onset risk of these diseases.

The agent for suppressing heart failure and the like of the present invention may be used not only as a medicine, but also as a quasi drug, a specified health food product, and a functional food product (an oral supplement, a health food product, a nutritional supplement food product, a hospital diet, a therapeutic diet and the like).

The medicine of the present invention may be formulated to various dosage forms by blending luteolin, a derivative thereof or a plant extract containing them with a pharmaceutical carrier as necessary. Examples of the dosage form include an oral preparation, an injection, a suppository, an ointment, a patch and the like, preferably an oral preparation. Examples of the oral preparation include tablets, granules, fine granules, powders, capsules, syrup and the like.

The pharmaceutical carrier includes various organic or inorganic carrier substances conventionally used as a formulation material, and is blended as an excipient, a binder, a disintegrator, a lubricant, a colorant or the like in a solid formulation; and as a solvent, a solubilization agent, a suspending agent, a tonicity agent, a buffer, a soothing agent or the like in a liquid formulation. In addition, a formulation additive such as an antiseptic, an antioxidant, a colorant, a sweetener and a stabilizer may be used as necessary.

In preparation of an oral solid formulation, luteolin, a derivative thereof or a plant extract containing them is added with an excipient, and as necessary, a binder, a disintegrator, a lubricant, a colorant, a flavoring agent, a corrigent or the like and then a tablet, a coated tablet, granules, powders, a capsule or the like may be manufactured in accordance with an ordinary method.

In preparation of an oral liquid formulation, luteolin, a derivative thereof or a plant extract containing them is added with a flavoring agent, a buffer, a stabilizer, a corrigent or the like and then an oral solution, a syrup, an elixir or the like may be manufactured in accordance with an ordinary method.

In preparation of an injection, luteolin, a derivative thereof or a plant extract containing them is added with a pH modifier, a buffer, a stabilizer, a tonicity agent, a topical anesthetic or the like and then a subcutaneous, intramuscular and intravenous injection agents may be manufactured in accordance with an ordinary method.

In preparation of a suppository, luteolin, a derivative thereof or a plant extract containing them is added with formulation carriers known in the art, for example, polyethylene glycol, lanolin, cacao butter, fatty acid triglyceride or the like, and further a surfactant such as Tween 80 (trademark) or the like as necessary and then the suppository may be manufactured in accordance with an ordinary method to.

In preparation of an ointment, luteolin, a derivative thereof or a plant extract containing them is blended with a base, a stabilizer, a wetting agent, a preservative or the like, which is usually used as necessary, mixed and formulated in accordance with an ordinary method.

In preparation of a patch, the above-mentioned ointment, a cream, a gel, a paste or the like may be applied onto an ordinary support with an ordinary method.

The amount of luteolin or a derivative thereof to be blended in the medicine or the functional food product described above varies depending on symptoms of a patient to be applied, the dosage form, and the like, but is generally about 0.05 to 1000 mg in an oral preparation, about 0.01 to 500 mg in an injection, and about 1 to 1000 mg in a suppository per dosage unit form.

In addition, the dose of the medicine having the dosage form per day varies depending on the symptoms, the body weight, the age, the sex and the like of a patient, and cannot be determined as a rule, but is usually about 0.05 to 5000 mg, preferably 0.1 to 1000 mg per day for an adult (60 kg body weight), and the medicine is preferably administered once or twice to three times or so in division per day.

In addition, luteolin-7-O-glucoside among the luteolin and a glycoside thereof has remarkably prompt and excellent oral absorption in comparison to luteolin or luteolin-7-O-apiosyl glucoside. Accordingly, a composition for oral intake comprising luteolin-7-O-glucoside is particularly useful as a composition for a medicine and a food product.

EXAMPLES

Hereinafter, the present invention is further specifically described with Examples, but the present invention is not limited to Examples.

Example 1

Angiotensin II was continuously infused to an 8 week-old male SD rat, and the action of luteolin glycoside (luteolin-7-O-glucoside was used) to cardiac fibrosis and cardiomegaly in the acceleration state of oxidative stress was investigated. For the control group, rats were normally raised. For the angiotensin II group (Ang II group), an angiotensin II-continuous infusion pump was implanted subcutaneously in the rat, and continuous infusion was performed for 7 days. For the luteolin glycoside simultaneous-administration group (Ang II+LMG group), a luteolin glycoside-blended feed (3.6 g of luteolin monoglycoside (LMG) was blended per 10 kg of feed) was fed for 3 weeks, then an angiotensin II-continuous infusion pump was implanted subcutaneously, and continuous infusion was performed for 7 days.

The blood pressure was measured at the seventh day, the degree of the ventricular wall thickness was evaluated with echocardiographic examination, then the heart was removed, and the weights of the heart and the ventricle were measured. The reactive oxygen was evaluated with hydroethidine staining, and the degree of fibrosis was evaluated with Masson's trichrome staining. Gene expressions of the fibrosis marker, and the heart failure marker in the ventricular tissue were evaluated with real time PCR.

Figure 2:
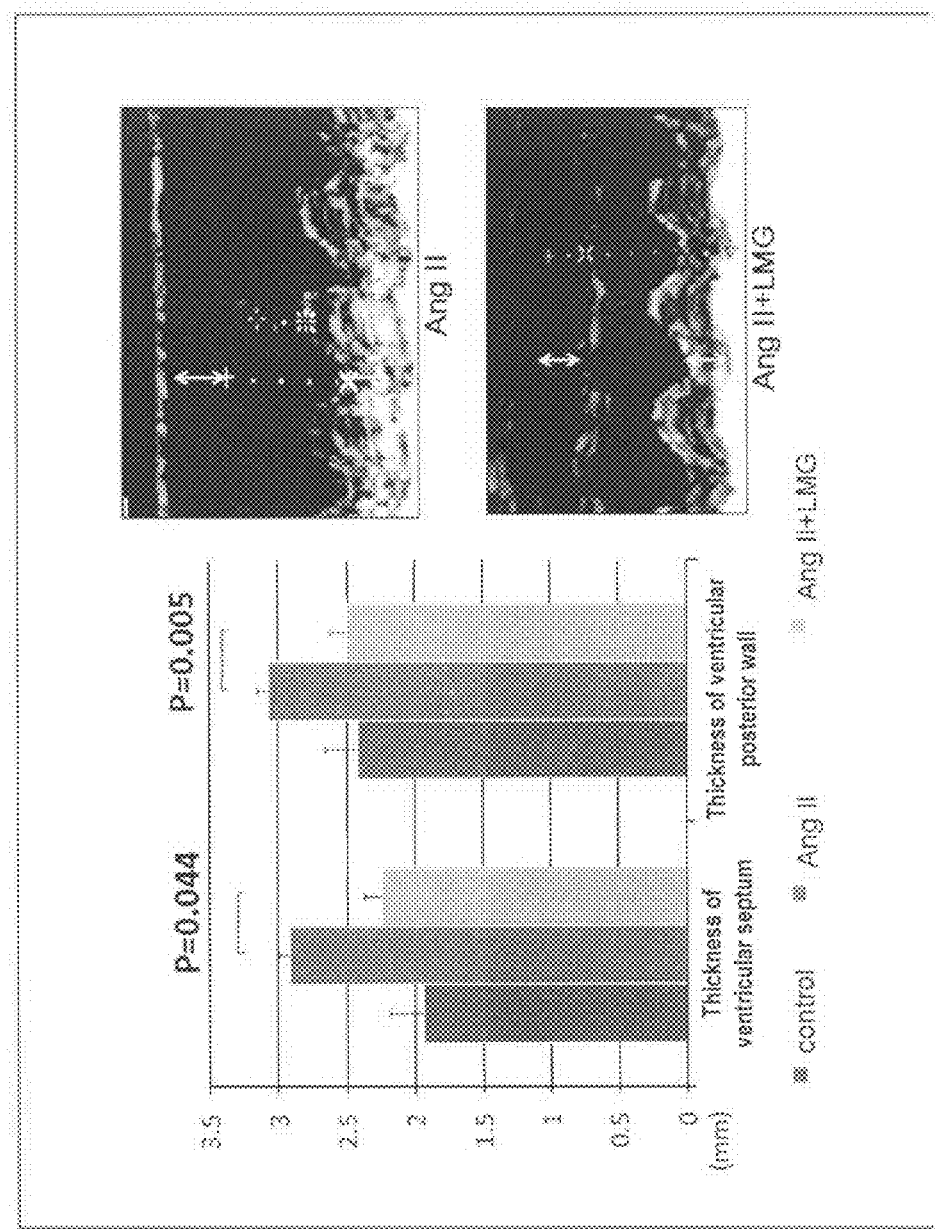
FIG. 2 illustrates the action of luteolin glycoside on ventricular wall thickening.
Figure 3:
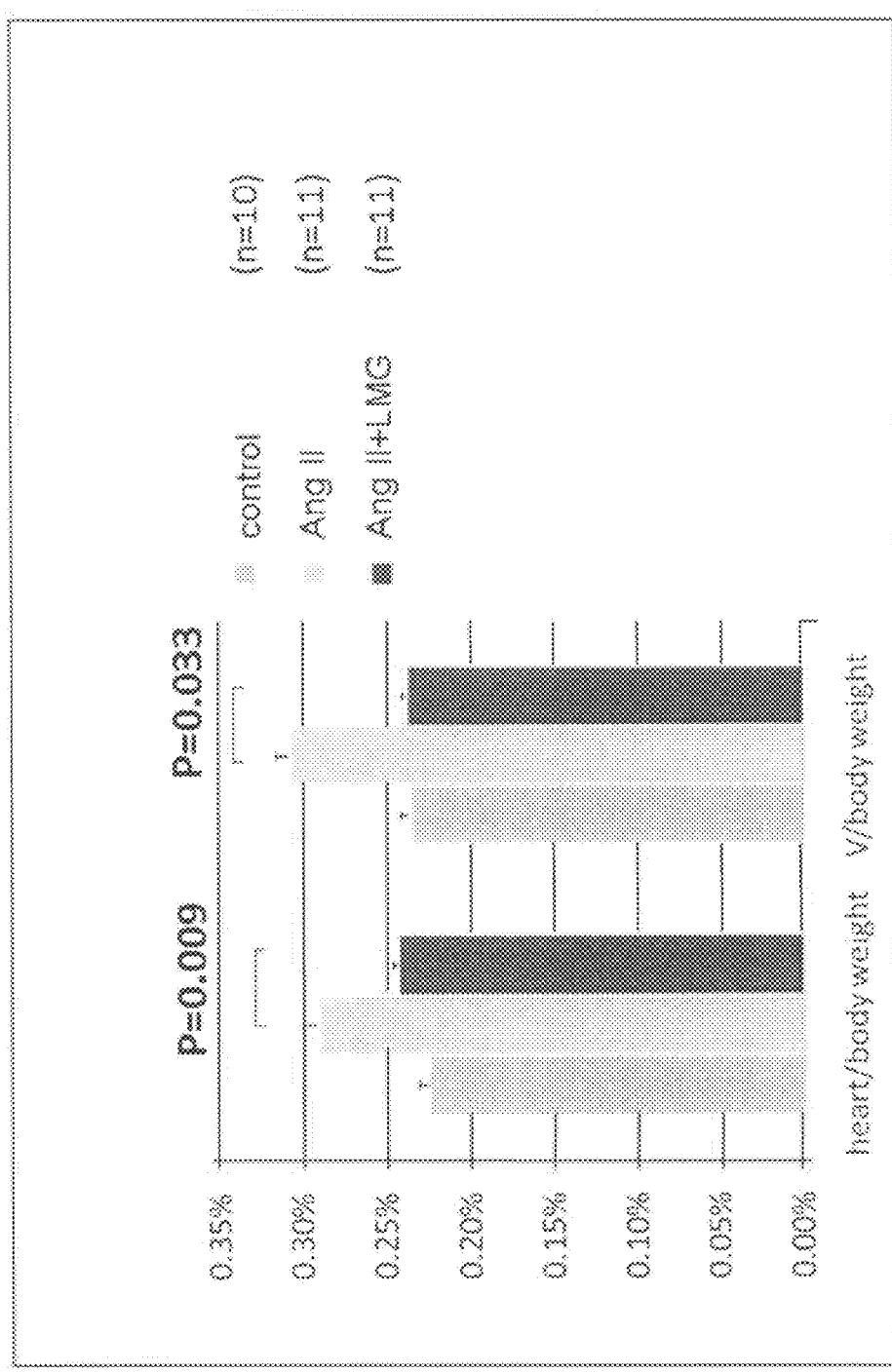
FIG. 3 illustrates the action of luteolin glycoside on the weights of the heart and the ventricle.

As a result thereof, the luteolin glycoside did not lower the blood pressure that was increased by the angiotensin II-continuous administration as shown in FIG. 1. In addition, as shown in FIG. 2, the ventricular wall thickening by the angiotensin II administration (Ang II) was significantly suppressed by administration of luteolin glycoside. As shown in FIG. 3, similar effects were observed in the evaluation for the heart weight and the ventricle weight. From these results, it is understood that luteolin glycoside has no influence on the blood pressure, acts effectively on the heart, and suppresses cardiomegaly.

Figure 4:
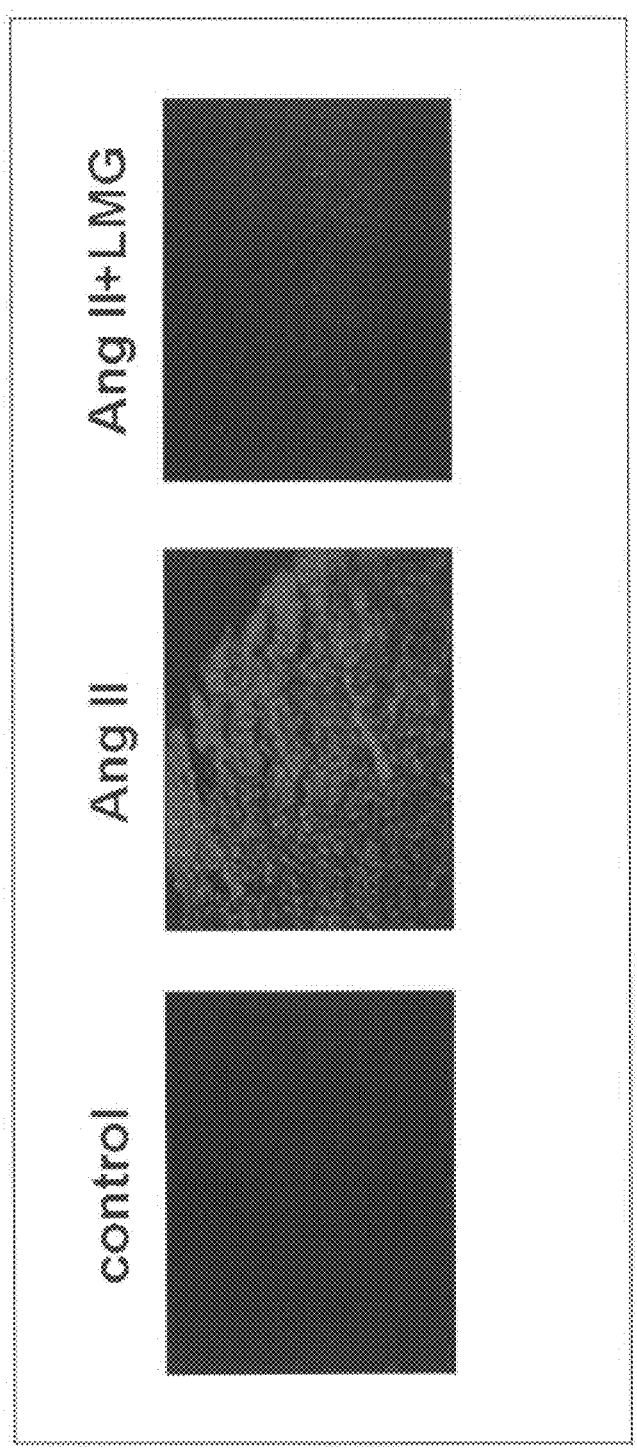
FIG. 4 illustrates the action of luteolin glycoside on reactive oxygen generation of the ventricular wall.
Figure 5:
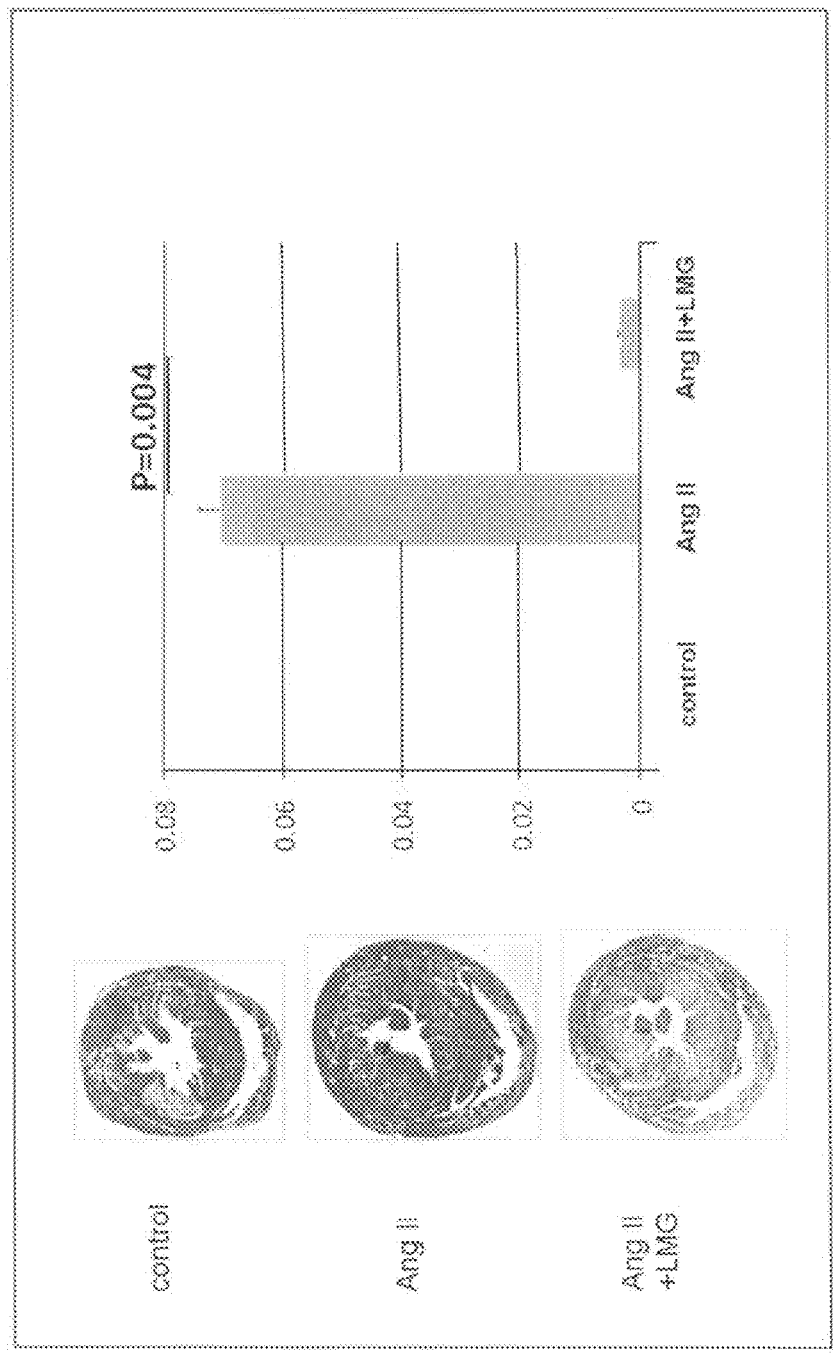
FIG. 5 illustrates the action of luteolin glycoside on fibrosis of the ventricular wall.

In addition, as shown in FIG. 4, luteolin glycoside remarkably suppressed generation of reactive oxygen in the ventricular wall by angiotensin II. Furthermore, as shown in FIG. 5, luteolin glycoside remarkably suppressed fibrosis of the ventricular wall by angiotensin II.

Figure 6:
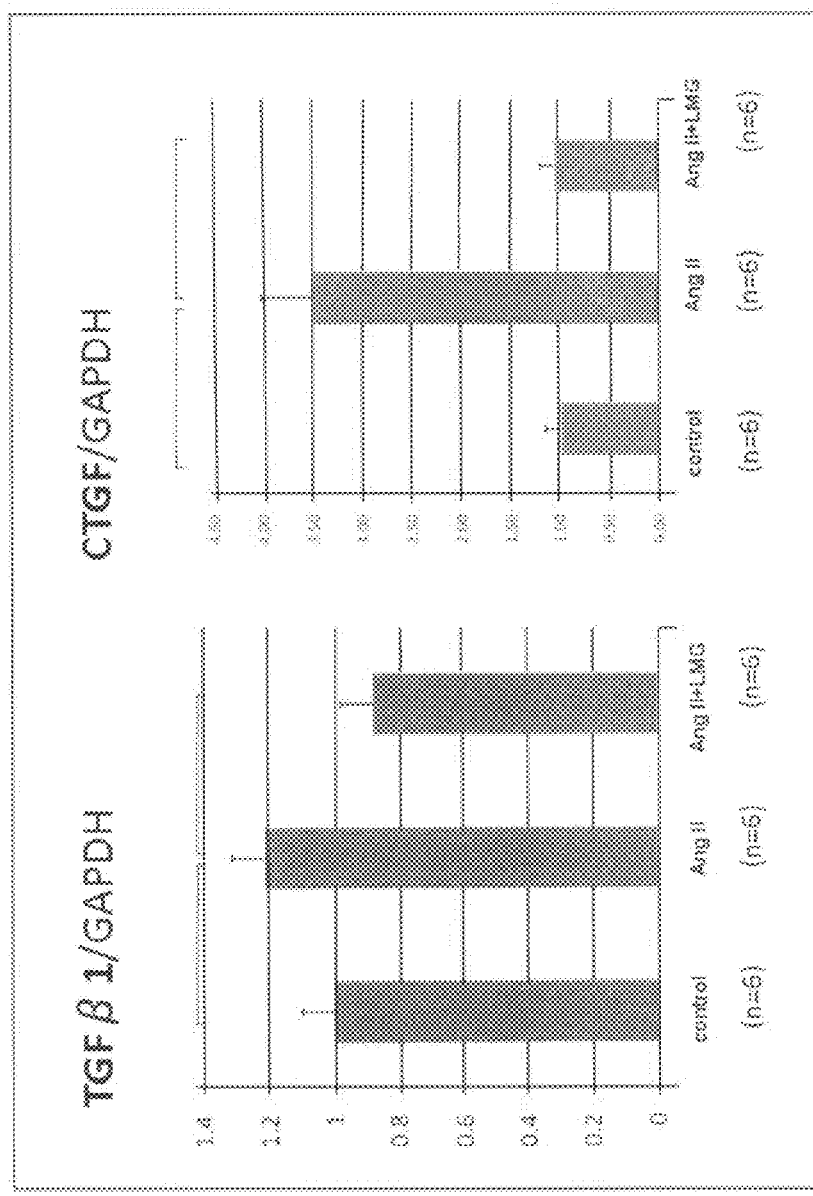
FIG. 6 illustrates the action of luteolin glycoside on expression of a marker gene for fibrosis of the ventricular tissue.
Figure 7:
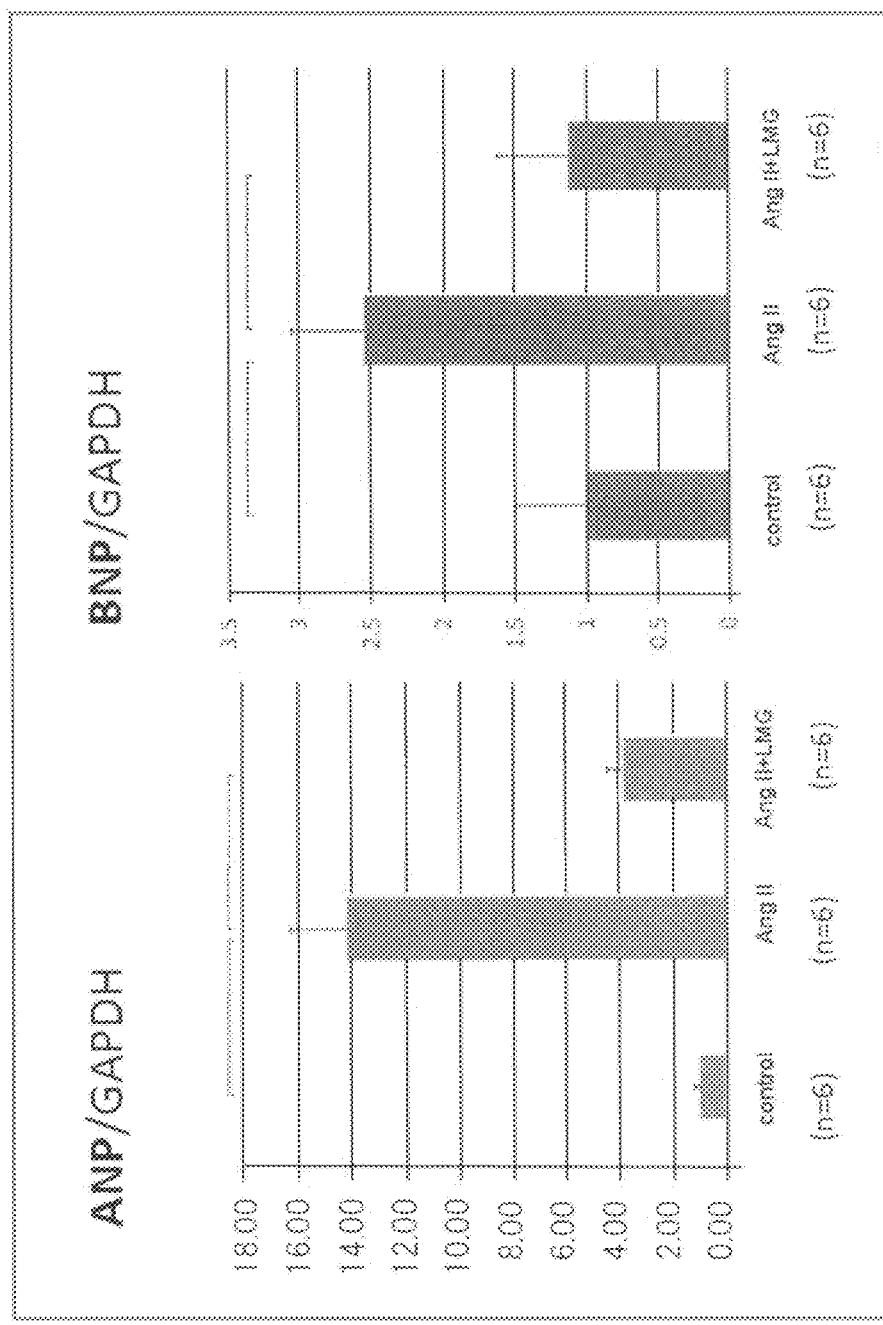
FIG. 7 illustrates the action of luteolin glycoside on expression of a marker gene for cardiomegaly and heart failure of the ventricular tissue.

RNA was extracted from the ventricular tissue, and expression amounts of various genes were evaluated with real time PCR. As shown in FIG. 6, with respect to gene expressions of TGF-β1 (transforming growth factor) and CTGF (connective tissue growth factor) that reflect fibrosis, activation of the expression by angiotensin II and suppression of the expression by combined use with luteolin glycoside were recognized even after correction with GAPDH expression of an internal standard, and these results corresponded to the degree of fibrosis (FIG. 5). As shown in FIG. 7, with respect to gene expressions of ANP (atrial natriuretic peptide) and BNP (brain natriuretic peptide) that reflect cardiomegaly and heart failure, activation of the expression by angiotensin II, and suppression of the expression by combined use with luteolin glycoside were recognized even after correction with GAPDH expression of an internal standard, and these results corresponded to the degree of cardiomegaly (FIGS. 2 3).

Example 2

Angiotensin II was continuously infused (for 16 weeks to 20 weeks) to a 12 week-old ApoE gene-deficient female mouse (ApoE−/−) (about 25 g of body weight) whereby to prepare an acute aneurysm model, and the action of luteolin glycoside (luteolin-7-O-glucoside was used) was investigated. For the control group (n=5), mice were normally raised (saline was continuously infused). For the angiotensin II group (Ang II tn-rmol group), an angiotensin II-continuous infusion pump was implanted subcutaneously in the mouse, and continuous infusion was performed for 4 weeks. For the luteolin glycoside simultaneous-administration group (Ang II+luteolin group), a luteolin glycoside-blended feed (0.055% of luteolin-7-O-glucoside was blended per feed) was fed for 3 weeks, then an angiotensin II-continuous infusion pump was implanted subcutaneously, and continuous infusion was performed for 4 weeks.

When the mouse was 20 weeks old, the blood pressure and body weight were measured, then the heart, the kidney and the aorta were removed, and generation of aneurysm was observed.

Figure 8:
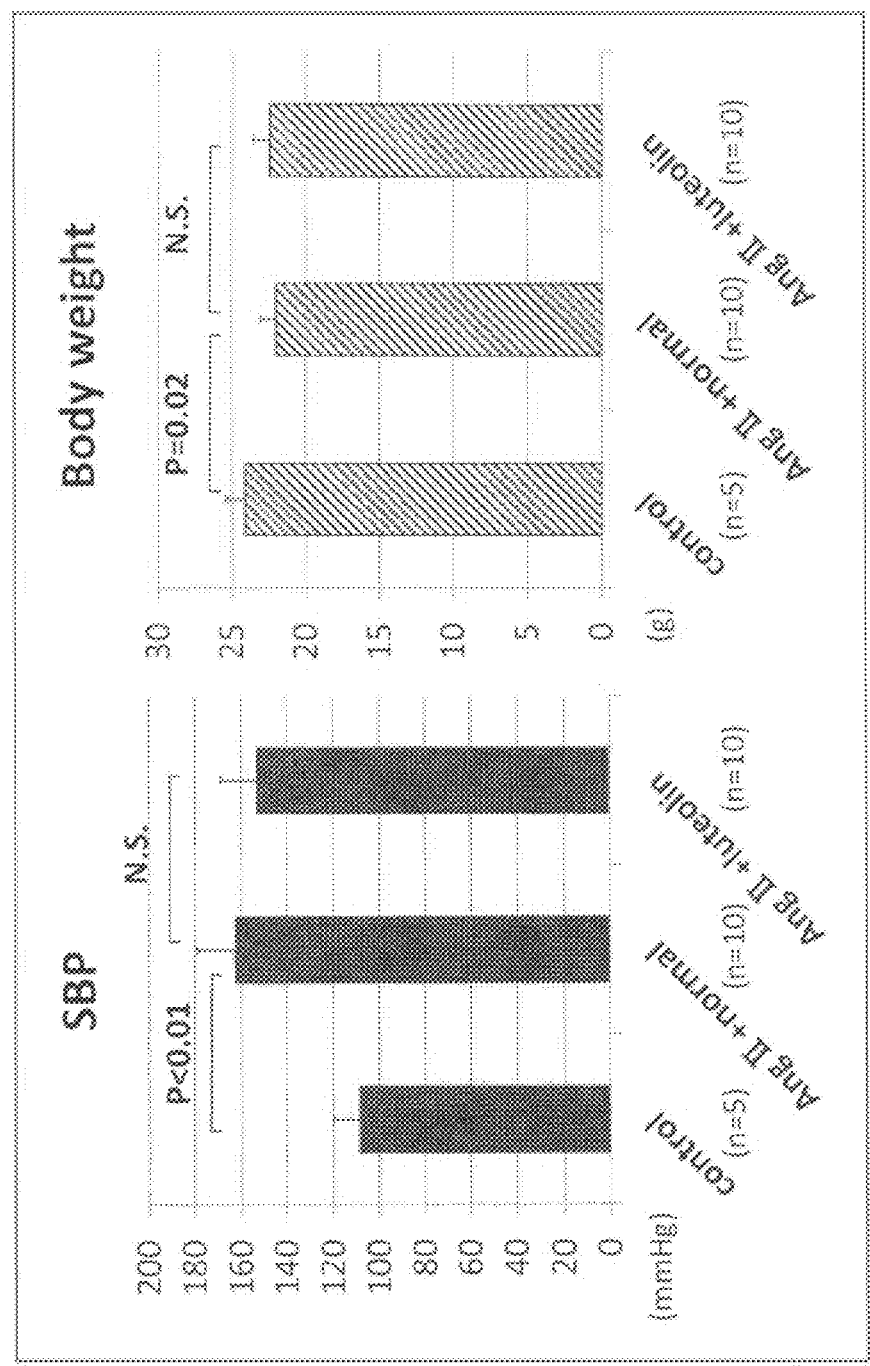
FIG. 8 illustrates the action of luteolin glycoside on the blood pressure and the body weight in a model of acute aneurysm.
Figure 9:
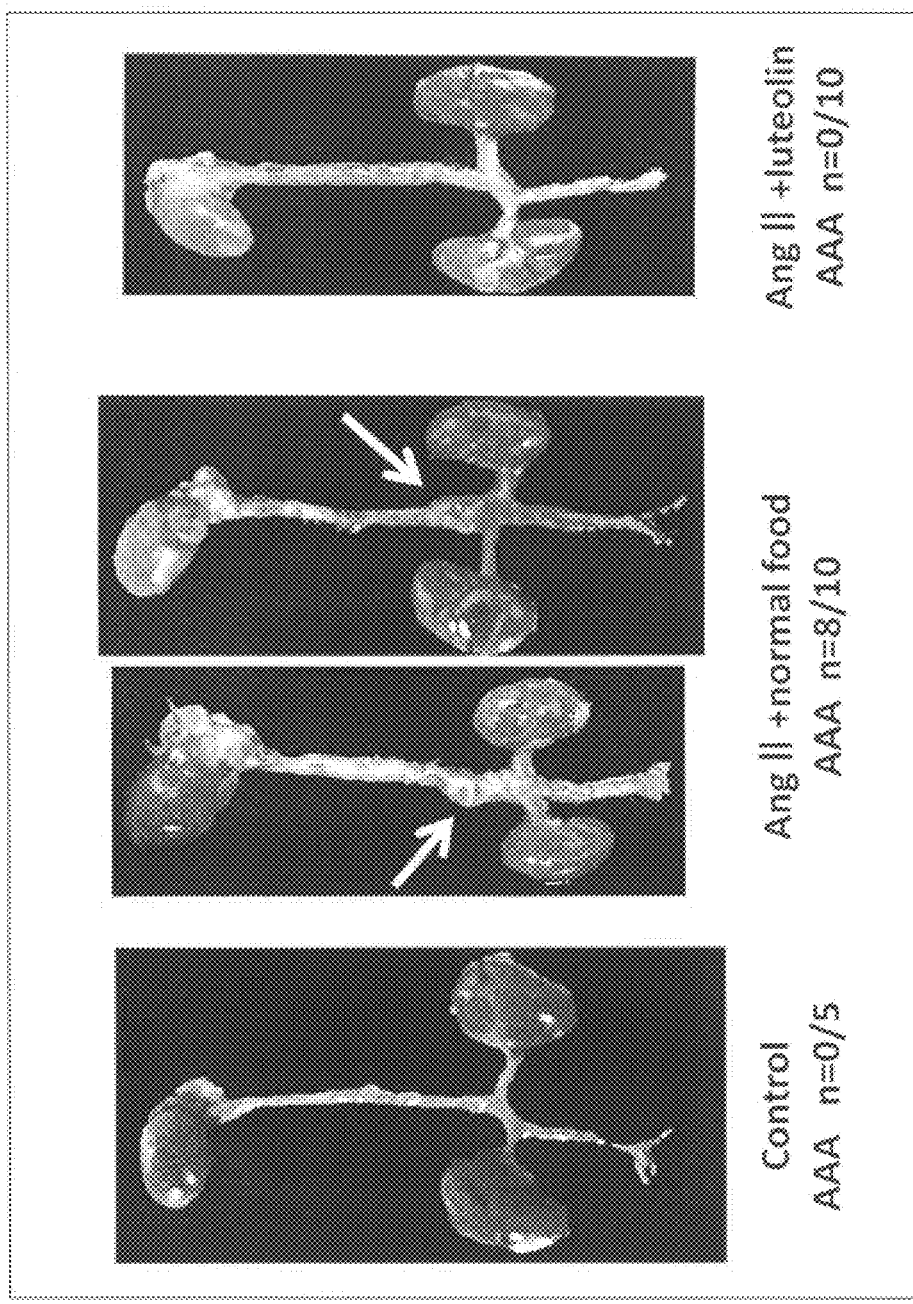
FIG. 9 illustrates the action of luteolin glycoside on aneurysm formation (appearance).
Figure 10:
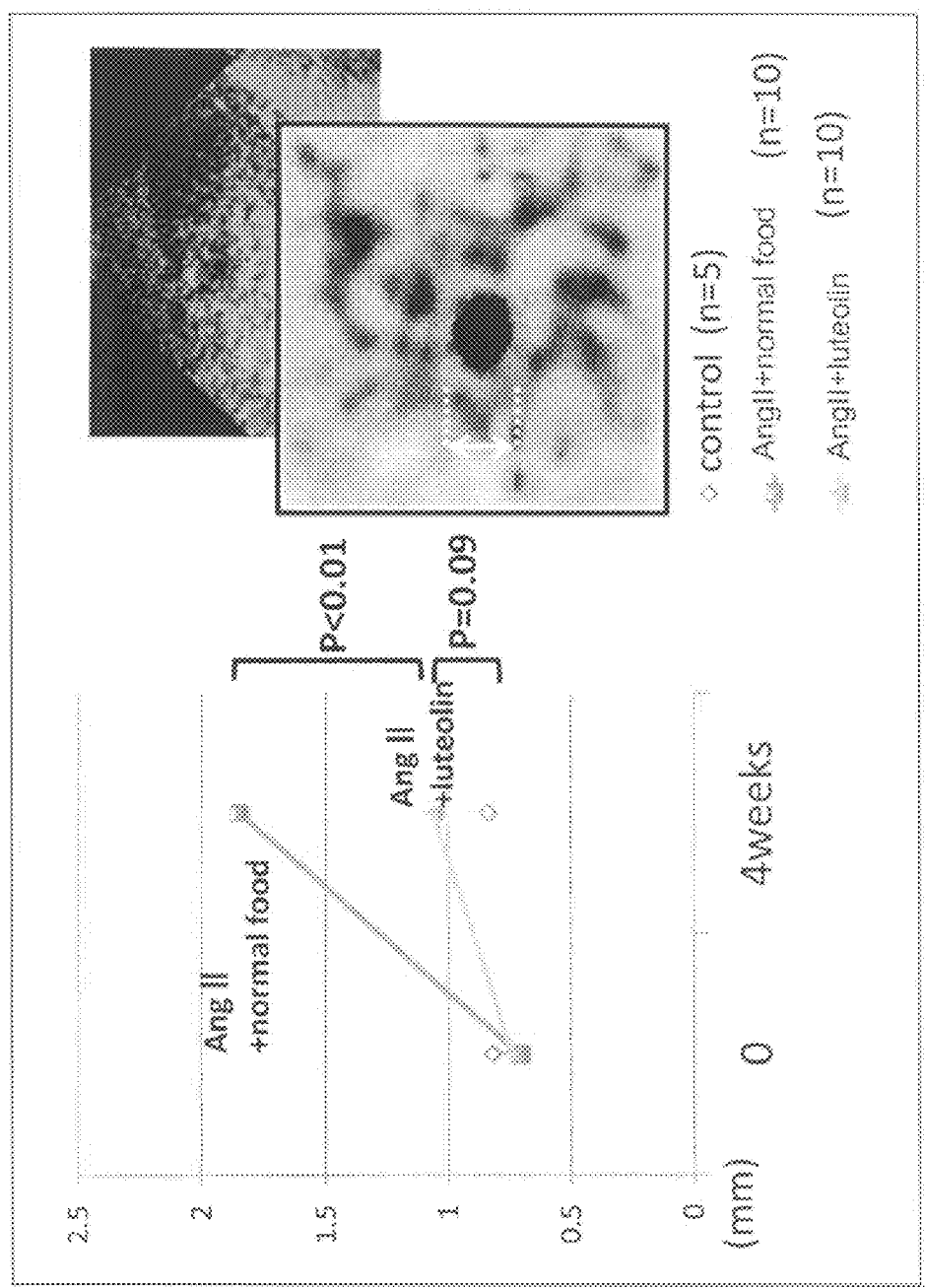
FIG. 10 illustrates the action of luteolin glycoside on aneurysm formation (diameter of the aneurysm).
Figure 11:
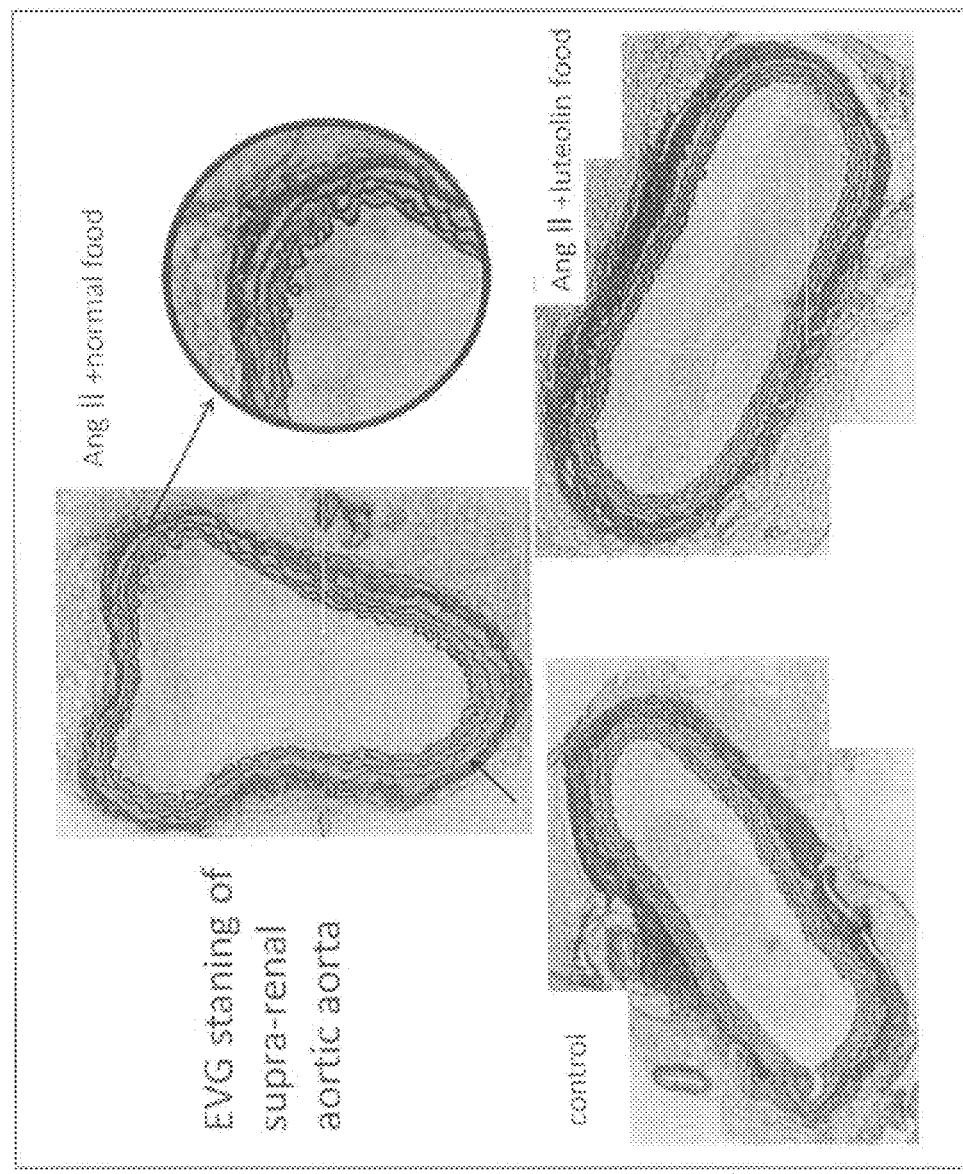
FIG. 11 illustrates the action of luteolin glycoside on aneurysm formation (effects of suppressing the rupture of the arterial wall elastic fiber).

As a result thereof, significant changes of the blood pressure and the body weight were not recognized in this dose of luteolin glycoside as shown in FIG. 8. As shown in FIG. 9, for the luteolin glycoside administration group, aneurysm formation was definitely suppressed. As shown in FIG. 10, for the luteolin glycoside administration group, the diameter of aneurysm decreased. In addition, as shown in FIG. 11, for the luteolin glycoside administration group, the rupture of the arterial wall elastic fiber was suppressed.

Example 3

Luteolin (51 mg/kg, PO), luteolin-7-O-glucoside (93 mg/kg, PO) and luteolin-7-O-apiosyl glucoside (175 mg/kg, PO) were orally administered to rats (8 weeks old, male SD rat), the blood was collected just before the administration, and at 0.5 hours, 1 hour, 2 hours and 8 hours after the administration from the tail vein, and the plasma luteolin concentration was measured. Meanwhile, the doses of each of the luteolin and a glycoside thereof were the same in terms of the amount of luteolin that is an aglycone.

The results thereof are shown in FIG. 12. As clarified from the results of FIG. 12, luteolin-7-O-glucoside exhibited remarkably higher oral absorption in comparison to luteolin and luteolin-7-O-apiosyl glucoside.

The invention claimed is:

1. A method of suppressing at least one heart disease selected from heart failure, cardiac fibrosis, ventricular wall thickening and cardiomegaly, the method comprising administering an effective amount of luteolin or a derivative thereof to a subject in need thereof, wherein the luteolin or a derivative thereof is a compound of formula (1):

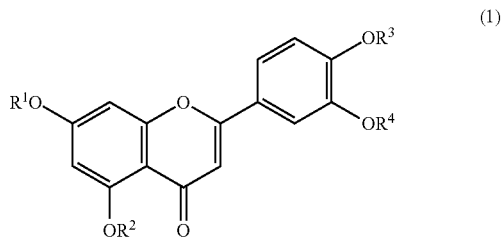

wherein $R^1$, $R^2$, $R^3$ and $R^4$ are each independently, a hydrogen atom, an alkyl group, a sulfo group or a sugar residue; and wherein said effective amount is an amount sufficient for said suppressing without influence on blood pressure.

2. The method according to claim 1, wherein the luteolin or a derivative thereof is luteolin.

3. The method according to claim 1, wherein the luteolin or a derivative thereof is luteolin-7-O-glucoside.

4. The method according to claim 1, wherein said alkyl group is a $C_{1-4}$ alkyl group.

5. The method according to claim 1, wherein said sugar residue is a monosaccharide or a disaccharide.

6. The method according to claim 1, wherein said sugar residue is an acetylated forms or a malonylated form of a sugar selected from the group consisting of glucose, galactose, xylose, mannose, glucuronic acid, apiosyl glucoside, maltose, cellobiose and gentiobiose.

7. The method according to claim 1, wherein said administering is orally.

8. The method according to claim 7, wherein said luteolin or a derivative thereof is in an oral preparation in an amount ranging from 0.05 to 1000 mg per dosage unit form.

9. The method according to claim 1, wherein said administering is by injection.

10. The method according to claim 9, wherein said luteolin or a derivative thereof is in an injection preparation in an amount ranging from 0.01 to 500 mg per dosage unit form.

11. The method according to claim 1, wherein said effective amount is 0.05 to 5000 mg per day per 60 kg body weight.

12. The method according to claim 1, wherein said sugar residue is selected from the group consisting of glucose, galactose, xylose, mannose, glucuronic acid, apiosyl glucoside, maltose, cellobiose, and gentiobiose.

13. A method of suppressing aneurysm, comprising administering an effective amount of luteolin or a derivative thereof to a subject in need thereof, wherein the luteolin or a derivative thereof is a compound of formula (1):

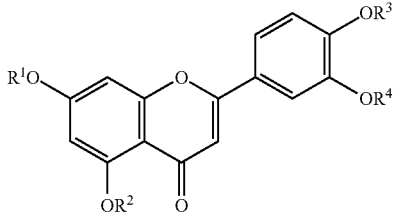

(1)

wherein $R^1$, $R^2$, $R^3$ and $R^4$ are each independently, a hydrogen atom, an alkyl group, a sulfo group or a sugar residue; and wherein said effective amount is an amount sufficient for said suppression without influence on blood pressure.

14. The method according to claim 13, wherein the luteolin or a derivative thereof is luteolin.

15. The method according to claim 13, wherein the luteolin or a derivative thereof is luteolin-7-O-glucoside.

16. The method according to claim 13, wherein said alkyl group is a $C_{1-4}$ alkyl group.

17. The method according to claim 13, wherein said sugar residue is a monosaccharide or a disaccharide.

18. The method according to claim 13, wherein said sugar residue is selected from the group consisting of glucose, galactose, xylose, mannose, glucuronic acid, apiosyl glucoside, maltose, cellobiose and gentiobiose.

19. The method according to claim 13, wherein said sugar residue is an acetylated forms or a malonylated form of a sugar selected from the group consisting of glucose, galactose, xylose, mannose, glucuronic acid, apiosyl glucoside, maltose, cellobiose and gentiobiose.

20. The method according to claim 13, wherein said administering is orally.

21. The method according to claim 20, wherein said luteolin or a derivative thereof is in an oral preparation in an amount ranging from 0.05 to 1000 mg per dosage unit form.

22. The method according to claim 13, wherein said administering is by injection.

23. The method according to claim 22, wherein said luteolin or a derivative thereof is in an injection preparation in an amount ranging from 0.01 to 500 mg per dosage unit form.

24. The method according to claim 13, wherein said effective amount is 0.05 to 5000 mg per day per 60 kg body weight.

* * * * *